(12) United States Patent
Branton et al.

(10) Patent No.: US 8,790,863 B2
(45) Date of Patent: Jul. 29, 2014

(54) ELECTRON BEAM PROCESSING WITH CONDENSED ICE

(75) Inventors: Daniel Branton, Lexington, MA (US); Anpan Han, Braband (DK); Jene A. Golovchenko, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/881,504

(22) PCT Filed: Oct. 26, 2011

(86) PCT No.: PCT/US2011/057805
§ 371 (c)(1),
(2), (4) Date: Jul. 3, 2013

(87) PCT Pub. No.: WO2012/099635
PCT Pub. Date: Jul. 26, 2012

(65) Prior Publication Data
US 2013/0288182 A1    Oct. 31, 2013

Related U.S. Application Data

(60) Provisional application No. 61/407,508, filed on Oct. 28, 2010.

(51) Int. Cl.
*G03F 7/38* (2006.01)
*B82B 3/00* (2006.01)
*G03F 7/16* (2006.01)

(52) U.S. Cl.
USPC .......... 430/296; 430/314; 430/315; 430/942; 216/58; 427/532; 427/551; 977/856; 977/857; 977/888; 977/890; 977/891

(58) Field of Classification Search
USPC .................. 430/296, 314, 315, 942; 216/58; 427/532, 551; 977/856, 857, 888, 890, 977/891
See application file for complete search history.

(56) References Cited

U.S. PATENT DOCUMENTS 7,435,353 B2 * 10/2008 Golovchenko et al. .......... 216/41
7,993,538 B2 * 8/2011 Golovchenko et al. .......... 216/41
8,273,257 B2 * 9/2012 Golovchenko et al. .......... 216/41

* cited by examiner

*Primary Examiner* — Christopher Young
(74) *Attorney, Agent, or Firm* — Theresa A. Lober

(57) ABSTRACT

In a method for imaging a solid state substrate, a vapor is condensed to an amorphous solid water condensate layer on a surface of a solid state substrate. Then an image of at least a portion of the substrate surface is produced by scanning an electron beam along the substrate surface through the water condensate layer. The water condensate layer integrity is maintained during electron beam scanning to prevent electron-beam contamination from reaching the substrate during electron beam scanning. Then one or more regions of the layer can be locally removed by directing an electron beam at the regions. A material layer can be deposited on top of the water condensate layer and any substrate surface exposed at the one or more regions, and the water condensate layer and regions of the material layer on top of the layer can be removed, leaving a patterned material layer on the substrate.

36 Claims, 4 Drawing Sheets

FIG. 3A
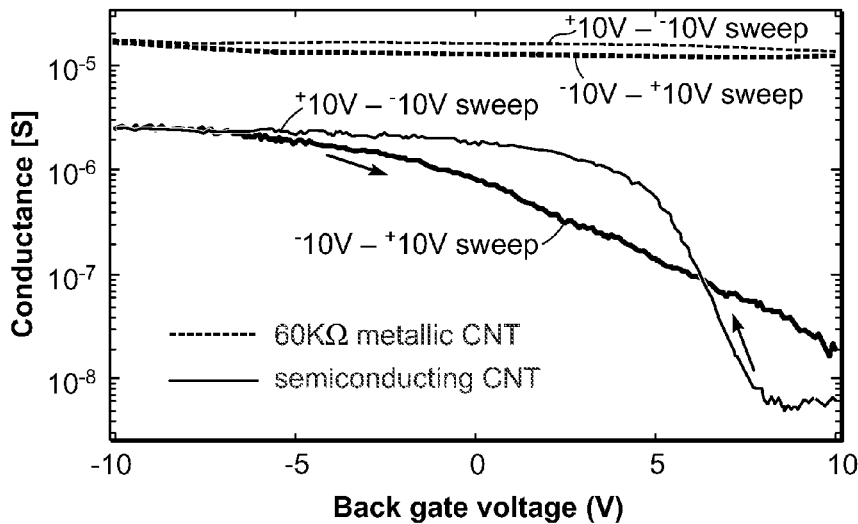
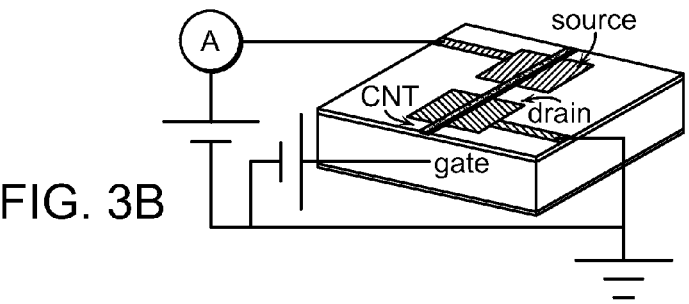
FIG. 3B
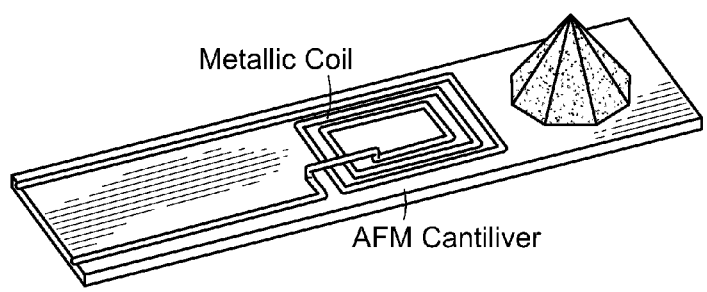
FIG. 4
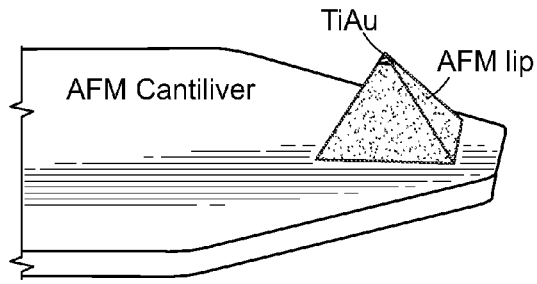
FIG. 5

ELECTRON BEAM PROCESSING WITH CONDENSED ICE

CROSS-REFERENCE TO RELATED APPLICATIONS

This application claims the benefit of U.S. Provisional Application No. 61/407,508, filed Oct. 28, 2010, the entirety of which is hereby incorporated by reference.

STATEMENT REGARDING FEDERALLY SPONSORED RESEARCH

This invention was made with Government support under Contract No. 5R014G003703 awarded by the NIH. The Government has certain rights in the invention.

BACKGROUND

This invention relates generally to imaging and lithography for microfabrication processes, and more particularly relates to electron beam imaging and lithographic processes.

Electron beam lithography (EBL or E-beam lithography) has become a critical tool for microelectronic fabrication processing and for nanoscience research. A wide range of applications, including microelectronics, nanoelectronics, optoelectronics, biological and biochemical sensing and analysis, and photovoltaic technologies all rely on EBL for the production of state-of-the-art systems. EBL is providing a step toward the resolution needed for nano-scale implementation of such devices and systems.

Conventionally, a lithographic process employing an electron beam is carried out with an organic photoresist, such as poly(methylmethacrylate) (PMMA). In one example of such a process, a microelectronic structure, such as a microelectronic substrate or wafer, is scanned with an electron beam to map the features on the structure and provide reference points for subsequent electron beam patterning of a layer of resist provided on the structure. Such a layer of resist, e.g., PMMA or other resist material, is then spun over the wafer. The resist layer is then exposed to a beam of electrons that is controlled to "write" a prespecified pattern of electrons across the layer surface. This direct writing of a pattern by an E-beam eliminates the need for a lithographic mask. The resist regions that are exposed to the E-beam writing pattern are irradiatively damaged, and during subsequent chemical development, are selectively removed. The unexposed resist regions remain on the wafer. Thereafter, a selected fabrication process, such as etching, metal deposition and lift-off, or doping, can be conducted with the patterned resist in place on the wafer, and the patterned resist subsequently removed, typically by a chemical solvent.

For many applications, the features that exist on a surface to be patterned by such an EBL process include non-planar, three-dimensional structures and topology and fragile structures, such as nanowires or single walled carbon nanotubes (SWCNTs), as well as fragile nanometric films such as graphene. For all of these features and materials, it is found that processing with an organic E-beam photoresist can produce residues that can contaminate devices and sensitize materials to contaminants, and can contaminate subsequent processes. Indeed, electron transport studies of very clean as-grown SWCNTs have demonstrated that organic resist contamination can obscure the intrinsic electrical properties of SWCNTs. Standard cleaning procedures for organic residue removal, such as oxygen plasma processes or highly oxidizing chemical treatments, have the unfortunate consequence that organic nanostructures, such as SWCNT and graphene, can themselves also be completely removed. As a result, conventional E-beam photoresist materials are often incompatible with the materials and structures for which EBL is required.

Even further, it is often found that E-beam mapping of a surface topology prior to E-beam patterning of a photoresist layer can damage or destroy features and topology on the surface. For example, SEM imaging of a carbon nanotube can accelerate contamination of the nanotube, can impact the intrinsic electrical properties of the nanotube, and may directly damage the nanotube. Imaging of such structures with an atomic force microscope (AFM) has been employed as an alternative to SEM imaging, but AFM imaging is conventionally extremely slow as well as highly inconvenient to integrate with an E-beam-based lithographic process. As a result, many nanoscale structures and materials cannot be imaged and/or patterned with conventional electron beam processes without perturbation of their native characteristics.

SUMMARY OF THE INVENTION

There is provided a method for imaging a solid state substrate that enables electron beam imaging and patterning while protecting the materials and structures being imaged and patterned. In the method, a vapor is condensed to an amorphous solid water condensate layer on a surface of a solid state substrate. Then an image of at least a portion of the substrate surface is produced by scanning an electron beam along the substrate surface through the water condensate layer. The water condensate layer integrity is maintained during electron beam scanning to prevent electron-beam contamination from reaching the substrate during electron beam scanning.

After production of the image, one or more regions of the layer can be locally removed by directing an electron beam at the regions. A material layer can be deposited on top of the water condensate layer and any substrate surface exposed at the selected one or more regions, and the water condensate layer and regions of the material layer that were deposited on top of the layer can be removed, leaving a patterned material layer on the substrate.

Condensed, amorphous water ice can serve as a protective coating for detailed imaging and spatial mapping of a substrate surface while preventing contamination from reaching the surface, and then further serve as a resist for high resolution E-beam lithography. The properties of water ice allow direct application in a vacuum environment, conformal coating of complex three-dimensional structures, through-resist mapping and registration of nanostructures, and simple, contamination-free removal. A wide range of device and system configurations and properties that heretofore were unattainable are thereby rendered achievable. Other features and advantages of the invention will be apparent from the following description and accompanying figures, and from the claims.

BRIEF DESCRIPTION OF THE DRAWINGS

FIG. 3A is a plot of measured conductance of a metallic carbon nanotube (CNT) and a plot of measured conductance of a semiconducting carbon nanotube as a function of back gate voltage for two different gate voltage ranges;

FIG. 3B is a schematic perspective view of a circuit configuration with a CNT for producing the data that is plotted in FIG. 3A;

FIG. 4 is a schematic perspective view of an example metallic coil produced on an AFM cantilever by the E-beam ice imaging and lithography process of FIGS. 1A-1F; and FIG. 5 is a schematic perspective view of an example metallic coating provided on the pyramidal tip of an AFM cantilever by the E-beam ice imaging and lithography process of FIGS. 1A-1F.

DETAILED DESCRIPTION

Methods described herein for E-beam imaging and lithographic patterning with a solid water condensate layer, or "water ice" are termed herein "electron beam ice imaging" and "electron beam ice lithography" (EBIL) for microfabrication processes. The EBIL cluster tool described herein enables the entire EBIL process to take place in the cluster tool. In the EBIL method, as explained in detail below, a vapor-deposited solid water condensate layer serves as a protective coating for enabling non-destructive E-beam imaging and mapping of features, structures, and surface regions underlying the coating of ice, through the ice, and further serves as both a resist for E-beam lithography subsequent to the imaging and/or mapping and a protective resist for processing of the underlying structures after patterning.

For many applications, it can be preferred to employ the EBIL cluster tool as provided herein for E-beam imaging and lithographic patterning all within a single vacuum system so that the entire EBIL process can be conducted and the process results examined within one vacuum system. A description of the cluster tool is provided in detail below. Referring to FIGS. 1A-1F, and to FIG. 2, the EBIL cluster tool 10 employs an E-beam field emission scanning and E-beam writing electron microscope (SEM) 34.

Figure 1A:
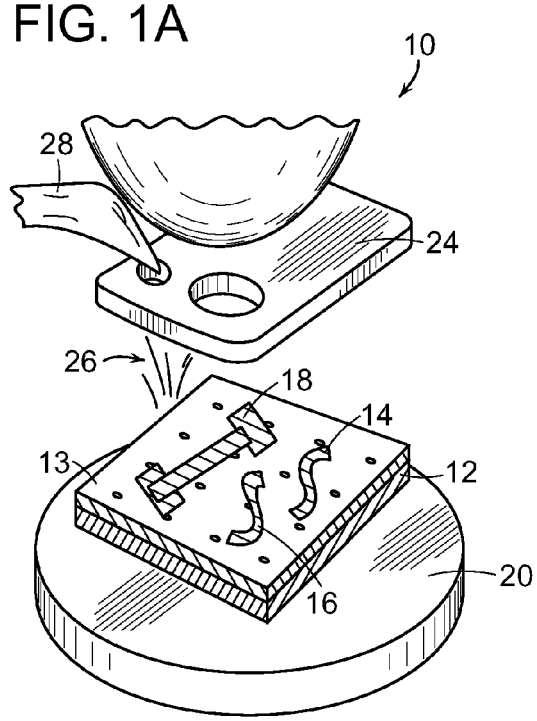
FIGS. 1A-1F are schematic perspective views of sequential processing steps in an example E-beam ice imaging and lithography process.

Referring to FIG. 1A, a solid state substrate, such as a microelectronic chip, wafer, or other platform or element formed of a solid state material such as a microelectronic material, or other substrate 12 that includes, e.g., a surface layer of structural features 14, 16, 18, is first cooled to a first selected temperature, e.g., cryogenic temperatures, in the microscope vacuum on a cryostage 20 of the SEM stage 22. A cold finger 24 or other element proximal to the SEM cryostage is provided to shield the cold sample from any but the intended condensable water molecules being deposited on the cold substrate surface. The substrate can be configured in as well as include three-dimensional mechanical configurations. The surface layer of features can include distinct meso-scale, micro-scale, and nano-scale elements, such as carbon nanotubes, three-dimensional micromechanical or microelectromechanical structures, including suspended and overhanging structures like MEMs beams, bridges, and cantilevers, and varying topological features, such as apertures, nanopores, and trenches, as well as planar electrical and/or mechanical elements. All such structural features can be disposed on the substrate surface and/or fabricated or synthesized directly on the substrate surface. The surface of the substrate can also include any number of surface layers 13 of various selected materials, in any desired pattern of materials and structural elements, and as explained below, can generally be preferred to include an insulating surface layer.

When the substrate 12 is cooled to a selected temperature for condensed-gas water ice formation, the structure 12 is exposed to water vapor 26 from a gas injection system 28. A thin, conformal layer of amorphous water ice 30, several tens of nanometers thick, forms on the surface of the structure, as shown in FIG. 1B. Details of amorphous ice deposition conditions and parameters to be controlled are given in detail below.

With the layer of ice 30 in place over the surface of the substrate 12, one or more regions of the substrate surface, or the entire substrate surface, is imaged through the ice layer. Distinct elements on the surface can be imaged, identified, and spatially mapped through the ice layer, to produce a spatial coordinate map of the surface features, as well as lithographic registration marks, and elements and regions of the surface can be analytically imaged. As shown in FIG. 1B, a field-emission E-beam 32 is controlled from the E-beam column 34 to scan the entire substrate 12 or a specified region or regions of the substrate to produce an image. The E-beam scan can be employed, e.g., to provide an image 36 of the substrate surface, including images of surface topology and structural features on the surface such as distinct surface structures 14, 16, 18. Features that are lying on, extending over, and/or supported by the substrate can therefore be imaged.

As explained in detail below, during imaging through the ice layer, the E-beam is preferably scanned along the surface while maintaining a relatively low intensity, that is, the E-beam dose during the scanning to produce an image is relatively low. This low-dose E-beam scanning does not to any significant degree impact the ice layer. Removal of the layer by the E-beam is thereby minimized during the E-beam scanning to produce an image. As a result, the ice layer provides robust protection of the substrate surface and surface features from the E-beam.

In generally, it is preferred that even if the ice layer is to some degree removed by the E-beam, the integrity of the layer is maintained sufficiently to prevent contamination from reaching the substrate during the electron beam scanning. The damage and contamination that is conventionally associated with direct E-beam exposure of many structures during E-beam imaging is thereby eliminated by E-beam imaging through the ice layer. Thus, even if a significant degree of the ice layer is removed during the E-beam imaging step, contamination is prevented from reaching the underlying substrate.

Figure 1C:
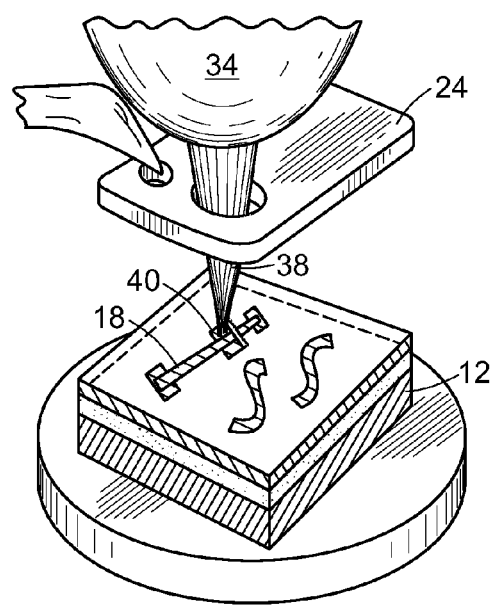
Figure 1B:
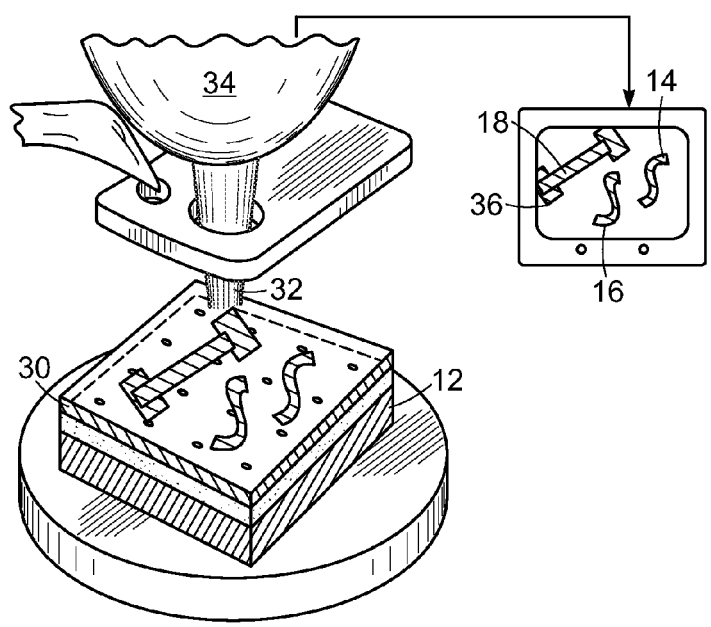

With imaging complete, the E-beam is then controlled to provide a focused, high-intensity beam of electrons 38 that is directed to a specific spatially-mapped location on the substrate surface, as shown in FIG. 1C. For example, the E-beam can be directed to a location 40 that is coincident with a selected feature 18 on the substrate surface that was identified and mapped during the E-beam imaging process. The E-beam control system of the SEM is directed to guide the E-beam to the selected site and to set an E-beam dose that is sufficient for removing the layer of ice at the selected site. The E-beam is therefore scanned only at the selected site or sites to remove the ice from that site or sites. This ice removal process can be conducted at various distinct, disconnected sites on the substrate surface.

The E-beam removal of the ice layer can be conducted to remove the ice layer through the full thickness of the layer, to produce a selected pattern of openings across the ice layer, in the manner of patterning a conventional photoresist, but without the need for the conventional steps used to develop the resist. The substrate surface and selected surface features are therefore exposed through openings at the selected sites by removal of the ice layer at those selected sites.

With ice layer patterning complete, the substrate surface can again be imaged in a low-dose E-beam scanning mode to inspect the quality of the patterning. The inspection imaging step can be conducted with the substrate in-place on the SEM cryostage, and therefore is particularly convenient. If this inspection indicates that the E-beam patterning is not satisfactory, additional ice resist can be allowed to condense on the surface to at least partially "remove" the pattern in the ice resist, without the need to remove or discard the substrate from the SEM cryostage. Thus, the E-beam patterning can be repeated multiple times, cycling between ice resist condensation and patterning, until E-beam image inspection determines that a pattern in the ice is completely satisfactory. Likewise, the ice layer condensation process itself can also be monitored in situ by a low-dose E-beam scanning, during the actual ice layer formation, to monitor the characteristics of the ice layer formation.

Figure 1D:
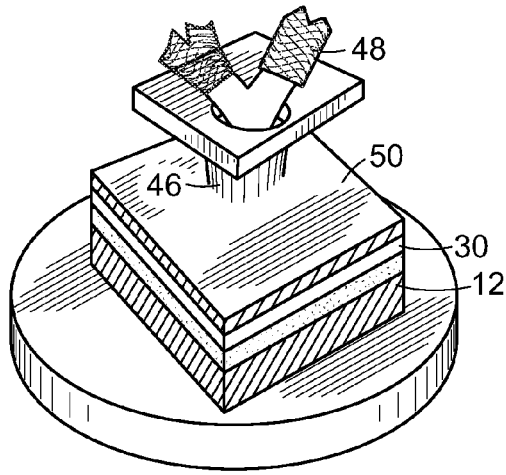
Figure 2:
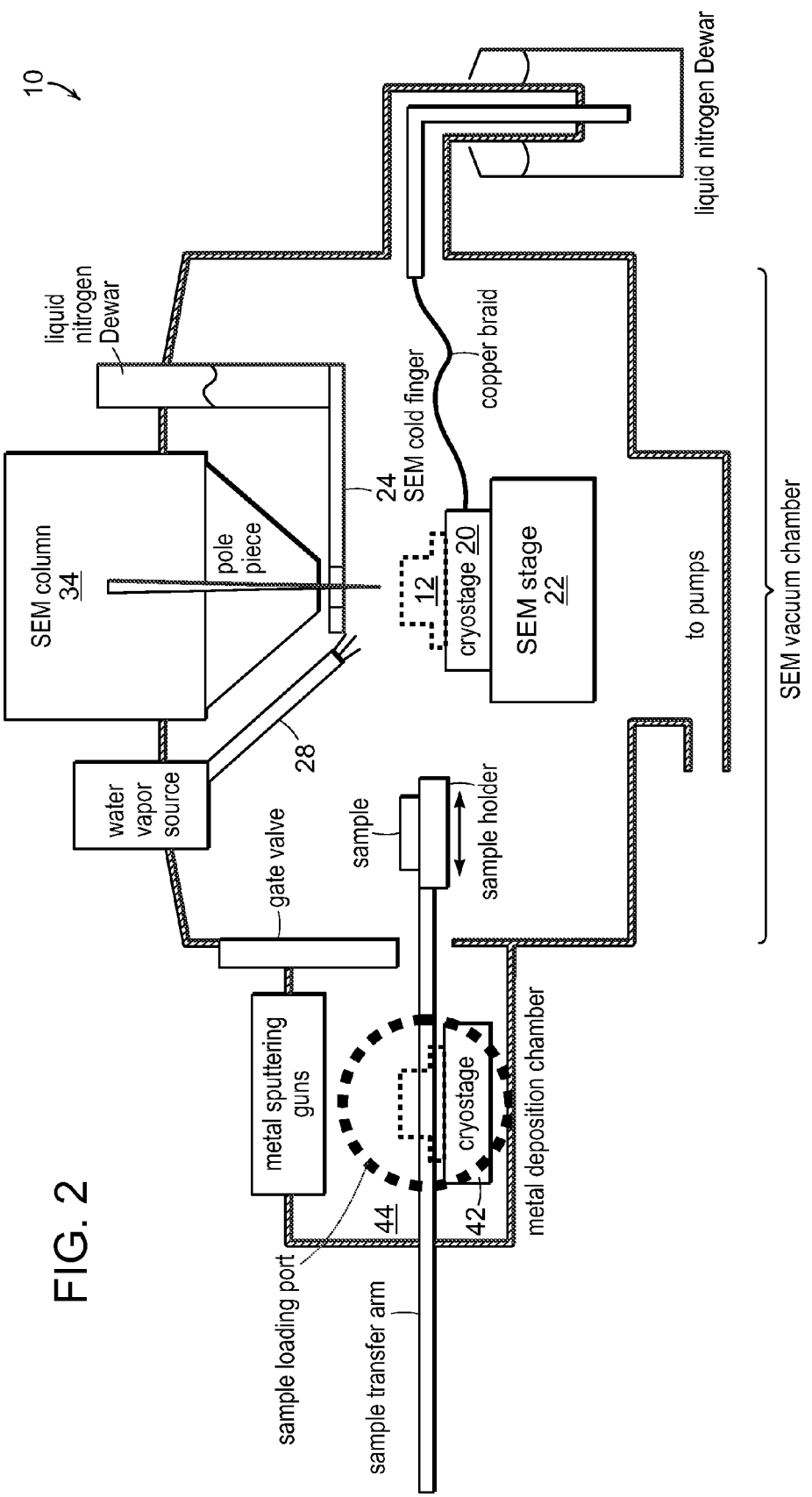
FIG. 2 is a schematic view of an example E-beam ice imaging and lithography process cluster tool.

Once any desired inspection imaging is complete, the substrate can then be rapidly transferred through the vacuum system onto a second cryostage 42 located in a separate chamber for processing of the substrate with the patterned ice layer in place. In one example, the separate chamber can be provided as a metal deposition chamber 44 in the cluster tool 10, as shown in FIG. 2. In such a metal deposition chamber, a selected metal 46 can be deposited, e.g., by plasma sputtering from sputtering guns 48, onto the ice-patterned substrate surface, as shown in FIG. 1D, to form a metal layer 50 atop the ice 30 on the substrate surface and on the substrate surface regions that are exposed through the patterned openings in the ice layer. Any selected number of different metals can be deposited, e.g., including an adhesion layer, that can be critical for noble metal adhesion onto dielectric surfaces. The metal or other material layer adheres to the substrate surface regions and features that are exposed through openings in the ice layer pattern, and deposits on the surface of the ice layer.

Figure 1E:
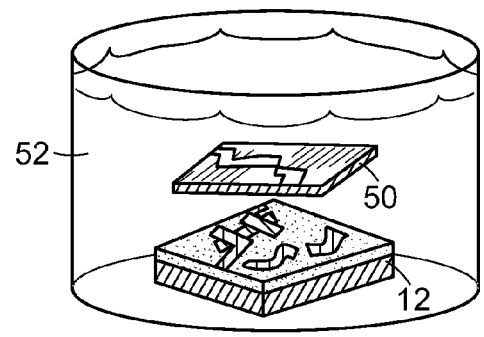
Figure 1F:
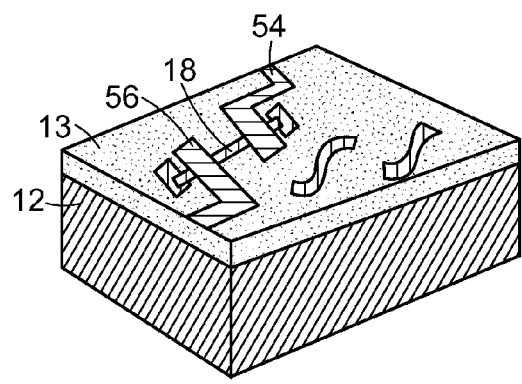

With a selected material in place over the ice layer, further processing of the substrate can be conducted within the cluster tool or external to the cluster tool. In one example, a lift-off process is carried out to form metal patterns on the substrate surface. In one example technique for such, as shown in FIG. 1E, the substrate is exposed to a selected environment, such as a room temperature liquid solvent environment, e.g., isopropanol, which lifts off the metal that is atop regions of ice while melting the ice, removing both the ice layer and the metal that is on the ice layer. The metal that was deposited through openings in the ice layer onto the substrate surface remains adhered to the substrate surface and is not removed from the substrate surface. As shown in FIG. 1F, this step results in a substrate 12 having surface features 18 that are processed, e.g., to provide metal contact regions 54, 56, to the features, with imaging, mapping, and processing of the features in a manner that does not damage or contaminate the features.

The lift-off of the solid condensate layer and upper material layer can be accomplished by techniques other than wet processing if desired. In one example technique, lift-off of the water ice layer and upper material layer is affected by conversion of the ice layer from the solid phase to the vapor phase in a process reversing the vapor-to-solid condensate formation of the layer. Such a solid-to-vapor process minimizes residue formation on the structure, minimizes liquid surface tension effects on the structure, and minimizes waste products. In situ sublimation of the ice layer can be accomplished by increasing the substrate temperature to a temperature at which the condensate layer sublimes. This in situ sublimation process can be controlled to enable a partial thickness reduction and/or complete layer removal. For example, an increase in substrate temperature to about 180 K at a pressure of less than $10^{-4}$ T is found to totally remove an ice condensate layer and enable lift-off of an upper metal layer, most reliably when the substrate is oriented so as to allow earth's gravity to attract metal deposited on the ice away from the substrate.

It is recognized that during a sublimation process there may be a formation of residue, such as minute deposits of the material layer, on the underlying structure. In such situation, it is preferred that a rinsing or cleaning technique be employed for removing such residue after the lift-off process is complete. It is further recognized that for some applications, in the course of sublimation of an ice layer an upper layer may trap the ice such that sublimation cannot proceed. For such a circumstance, it can be preferred to provide access apertures in the upper layer or the substrate such that sublimation of the ice layer can be enabled. The complete sublimation of a solid ice layer in a multilayer system can then be accomplished. Where the sublimation temperature or time characteristic of a given ice layer are not practical for a given application, the ice layer can be removed by a process other than sublimation or wet processing. For example, vapor processing or other conventional layer removal process can be employed. In addition, a low-dose E-beam scan across the layer can for selected conditions fully remove all portions of the layer.

Turning back to the EBIL process sequence, after completion of selected processing steps and removal of the patterned ice layer, the substrate 12 can again be introduced to the cluster tool and, as in FIG. 1A, a new layer of ice can be formed over the substrate. The substrate can then again be imaged, as in FIG. 1B, at a low-dose E-beam setting as explained above to non-destructively inspect the results of the fabrication sequence by E-beam scanning of the entire substrate surface or selected regions of the substrate surface without removing the ice layer. This last imaging step can be particularly effective for evaluating the completed devices without damage and with prevention of contamination reaching the devices. With such imaging complete, the ice layer is then removed from the substrate, e.g., by sublimation, by immersion in an alcohol bath, or by conventional microfabrication cleaning techniques.

With this EBIL process and cluster tool, the conventional E-beam lithographic processes of mapping of substrate surface features and/or lithographic pattern registration marks, organic photoresist spinning on the imaged substrate, resist baking, E-beam exposure of the photoresist, chemical development of the resist, and metal evaporation, which require six different instruments, can be accomplished by the EBIL process in one instrument, the EBIL cluster tool. The E-beam imaging and lithography processes are thereby greatly simplified as well as streamlined. Labile nanostructures, such as carbon nanotubes, can be safely imaged by the E-beam through the ice protective layer without contamination or damage, by maintaining the integrity of the ice layer during electron beam scanning. The ice protective layer can then be exploited as a resist layer and accordingly can be patterned at a corresponding E-beam intensity. The patterned ice film then serves as a mask, e.g., as a mask for a lift-off process. The ice film enables the lift-off without device degradation and contamination that is commonly associated with E-beam imaging and polymer resist residues. Additional layers of ice can be provided for imaging at subsequent points in the process and at the end of the fabrication sequence.

As explained above and shown in FIG. 1B, it is conventional in E-beam processing to first image and spatially map a substrate surface to locate the site or sites of interest for E-beam lithography as well as to define the spatial coordinates of feature positions and registration marks across the substrate surface. For many applications, it is required to identify the location of a nanostructure of interest by E-beam mapping of the structure. For example, in the fabrication of carbon nanotube-based devices, there can be required an electrical connection of a carbon nanotube to a metal contact pad on a substrate surface. The carbon nanotube of interest must first be located on the substrate and its spatial position mapped for patterning of a resist layer in production of a metal layer between the nanotube and the contact pad. In the EBIL method, such mapping is conducted through a layer of ice resist that is provided over the substrate surface, preferably at an E-beam intensity that removes substantially no ice during the imaging. The ice resist thereby enables full and complete imaging of features under the ice, with the ice maintained at cryogenic temperatures to maintain its integrity to protect the features and substrate surface from contamination that conventionally is produced by E-beam imaging.

It is found experimentally that features underlying an ice layer can be imaged by a low-energy, low-dose E-beam scan through the ice layer to produce an image that is as accurate as an image produced by an E-beam scan across a substrate having no protective ice layer, and even as accurate as an image produced by an AFM scan across a substrate having no protective ice layer. It conventionally takes about four hours to image and map a 50×50 µm area with an AFM. With the low-dose, low-intensity E-beam scan of the EBIL process through an ice layer, this area can easily be mapped in a few minutes, and can be maintained with sufficient integrity to provide the same accuracy in imaging without the damage and contamination that are typically associated with E-beam scanning reaching the substrate.

Considering the imaging of specific features, such as nanostructures, through an ice layer, contrast in an E-beam image of a nanostructure such as a nanotube is the result of dynamic charging of electrically insulating layers by the incident E-beam. Specifically, electrical charge of the E-beam is deposited in electrically insulating materials and structures present on a substrate being imaged. Secondary electrical charge flows from the insulating materials and structures to more highly electrically conductive materials and structures. The more highly-conductive structures thereby distinctly appear in an E-beam image due to collection of electrical charge at those structures.

The ice layer formed atop a substrate surface layer is electrically insulating and operates as an electrical insulator for E-beam imaging purposes. It is therefore preferred that substrate structures or features to be imaged be characterized by a higher degree of electrical conductivity than the ice layer. It further can be preferred for imaging distinct structures and features that there be provided a substrate surface layer underlying the surface structures or features that itself is also insulating, e.g., a layer of oxide, such as $SiO_2$, or nitride, such as $Si_3N_4$, to cooperate with the ice layer as a charged insulating region for E-beam imaging.

The ice and substrate insulating layers become negatively charged by exposure to the primary E-beam and the more highly electrically conducting structures, such as carbon nanotubes, remain at a lower potential, e.g., electrical ground potential. Such electrical grounding of surface structures can be implemented by connection to a substrate surface contact pad or other contact, e.g., carbon nanotube catalyst pad, for making connection to electrical ground through, e.g., the substrate and stage on which the substrate is supported. Consequently, low-energy secondary electrons emitted near the electrically conducting structures are collected by the conducting structures rather than the E-beam secondary electron detector. This visibly distinguishes the conducting structures as darker than the charged, insulating materials.

It is not required that all surface structures or features to be imaged be connected to electrical ground. Connection of a surface feature, such as a carbon nanotube, to a surface metal electrode, that is not connected electrical ground still provides a large electrically conducting reservoir for charge dissipation and thus, enhances image contrast. Depending on the E-beam characteristics, the ice resist thickness, the thickness and insulating properties of substrate surface layers below the ice layer, and the substrate potential, imaging of structures of a wide range of electrical conductivities can be achieved through the ice layer for a wide range of grounding conditions.

It is found that in general, the ranges of E-beam energy and dose for imaging a surface through a layer of ice without damaging labile structures, such as carbon nanotubes or graphene, are in the range of about 1-50 kV for the beam energy and an E-beam dose not exceeding about 100 µC/cm$^2$ for many imaging applications not exceeding 500 µC/cm$^2$ for high-resolution imaging applications. With this condition, removal of ice is minimized. For any E-beam energy, it is found that the dose required to image a structure through a layer of ice is generally about two or three orders of magnitude less than the dose require to remove a region of the ice layer, and can for many applications be more than 1000 times less than the dose required to remove portions of the ice layer. It is therefore preferred that a structure be imaged through an ice layer at a first E-beam dose that is at least two orders of magnitude than a second E-beam dose that is employed for removing regions of the ice layer. Under these conditions, substantially no ice layer is removed by the E-beam imaging process. But as stated above, even if some of the ice layer is removed, the integrity of the ice layer is maintained at the deposition temperature to prevent contamination from reaching the substrate.

It is to be recognized that the beam energy for satisfactorily imaging conducting nano-scale features and structures such as carbon nanotubes through an ice layer depends in general on the ice layer thickness, the composition of the substrate, and the electrical biases on the carbon nanotube catalyst pad and the substrate, such as a silicon back gate. It is found that for a given thickness of ice there exists an optimal imaging energy through an ice layer, where "optimal" herein means an ability to achieve images in which one can see what is necessary for the fabrication purpose at hand. For example, in the case of carbon nanotubes, it can be important to produce an image with contrast of the nanotubes so that the nanotubes can be imaged in a low resolution E-beam image, or alternatively, it can be important to see very closely-spaced nanotubes, for which one may require a higher resolution E-beam image. If the E-beam energy is too low or too high, no carbon nanotube image contrast can be obtained through the ice. It can therefore be preferred to empirically determine an optimal ice layer thickness for a given imaging application.

To provide an example of how parameter control can be employed for EBIL imaging, here using the example of carbon nanotubes, Table I below summarizes the E-beam imaging parameters for several configurations having the specified electrical state. E-beam current affects the electron flux hitting the substrate. The dose is the number of electrons, expressed in µCoulombs/cm$^2$, required for producing one image by scanning the E-beam over a 60 µm by 45 µm area.

TABLE I

| substrate | CNT catalyst pad potential | Si back gate potential | ice thickness (nm) | beam energy (kV) | beam current (pA) | dose (μC/cm$^2$) |
|---|---|---|---|---|---|---|
| Si substrates coated with 300 nm of SiO$_2$ | Ground/ Float | Ground/ Float | 0-500 | 1.8-2 | 10-20 | 25 to 50 |
| Si substrates coated with 500 nm of SiO$_2$ and then 60 nm Si$_3$N$_4$ | Ground/ Float | Ground | 0-1000 | 2, 3, 4, 5 | 10-20 | 25 to 50 |
| 60 nm Si$_3$N$_4$ membranes | Ground/ Float | Ground | 0-1000 | 3, 4, 5 | 10-20 | 25 to 50 |

For a given substrate condition, it is found that the E-beam energy required for useful imaging increases with thickness of the ice layer. The preferred voltage for optimal imaging contrast, for a given application, varies with the substrate conditions. For example, as just explained, the electrical potential of the substrate and the nanotube catalyst pads have a strong influence on the appearance of a carbon nanotube in an E-beam image. Further, as an ice layer thickness is increased, surface structures such as a carbon nanotube can become completely obscured, but with a slight increase in E-beam acceleration voltage, the image contrast of such structures through the ice layer is restored. Thus, with the appropriate combination of beam energy, electrical conductor potential, and substrate potential, a desired image of a structure such as a carbon nanotube can be obtained for a selected ice layer thickness. Accordingly, the precise positioning of carbon nanotubes and other surface structures can be determined and mapped for subsequent process steps.

With this imaging process, ice removal by the E-beam is minimized and no significant ice removal occurs as an E-beam is scanned across an ice-coated substrate to image the surface of the substrate. As explained above, the E-beam dose required for imaging through an ice layer is at least two orders of magnitude smaller than that required for actual patterning of the ice layer, and as a result, the ice layer provides a robust barrier against damage and contamination to the underlying structures. Thus, aside from the time saving aspects of the in situ EBIL imaging, it is found that the E-beam damage and contamination that have conventionally limited the usefulness of SEM mapping are avoided by the ice layer imaging process of the EBIL method.

After imaging structures through the ice layer at a first E-beam dose, patterned ice removal can be conducted at a second E-beam dose that is at least two orders of magnitude greater than the E-beam dose employed for imaging. For example, given an E-beam energy of, e.g., about, 20 kV, a dose of only about 100 μC/cm$^2$ can be employed for many application for imaging through an 80 nm-thick ice layer, with a dose of about 1 C/cm$^2$ employed to remove a portion of the 80 nm-thick ice layer. After the E-beam patterning of the ice layer, the substrate surface can be immediately imaged again, at the first, lower imaging intensity, to inspect the pattern quality in the ice layer with a low E-beam dose. Such inspection, which is not possible with standard lithography, provides a valuable opportunity to make minor corrections, either by further patterning or be additional ice layer condensation, or to abort further processing.

Therefore, in one example process, the E-beam dose is first controlled to provide a low imaging dose for mapping structures on a substrate through an ice layer, minimizing ice resist removal; then the E-beam dose is controlled to produce a high patterning dose, at least two or three orders of magnitude higher than the imaging dose, and at least 1000 times higher for some applications, for patterning an ice layer after imaging; and then the E-beam dose is again controlled to produce a low imaging dose for inspecting the ice layer patterning. A cyclic process of repeated ice layer patterning and ice layer imaging can be conducted to in situ monitor E-beam writing of a pattern in an ice layer and correction, enhancement, or extension of a pattern determined in real time and carried out with further imaging if desired, all on the SEM cryostage.

Once patterning of the ice layer is complete, the ice layer is preferably maintained at an appropriate temperature that maintains the ice layer integrity during processing of the substrate. For example, the patterned substrate can be transferred onto a metal deposition cryostage held at, e.g., 165 K. At this temperature, 14 nm of ice sublimes in 1 min. It can be preferred to allow some ice to sublime to ensure that all ice is removed from the bottom of the ice resist pattern. For example, five nanometers of ice can be allowed to sublime from the entire sample surface to assure that any remaining ice remaining at the bottom of the patterned mask wells from the patterning step is removed before depositing metals. After metal deposition, lift-off can be carried out in, e.g., isopropanol, as shown in FIG. 1E.

Thus, one example EBIL process for carbon nanotube processing can be summarized by the steps illustrated in FIGS. 1A-1F as follows. A substrate with, e.g., pre-formed Mo micro-leads and carbon nanotubes on a SiO$_2$ surface layer is loaded into the SEM of the EBIL cluster tool of FIG. 2 via the load-lock and cooled down to ~110 K on the SEM cryo-stage. Water vapor is leaked into the SEM through a nozzle just above the sample and condenses as amorphous ice on the cold sample. Typically, 80 nm of ice is deposited in 30 under these conditions. The location of carbon nanotubes under the ice is then mapped by E-beam scanning of the ice-coated substrate at low E-beam energy and low dose, not exceeding about 100 μC/cm$^2$, to identify a carbon nanotube of interest.

This nanotube imaging can be particularly effective for applications, e.g., in which a plurality of nanotubes are synthesized at the site of a device and then one of the synthesized nanotubes is to be selected for connection at the device. This carbon nanotube synthesis and selection process can be conducted as described in US2009/0136682, published on Apr. 28, 2009, the entirety of which is hereby incorporated by reference. Imaging of a plurality of nanotubes that are synthesized from a catalyst pad in the vicinity of one or more nanopores can be conducted through the ice layer to determine which nanotube is most closely aligned with a selected nanopore.

Once a nanotube is selected by imaging through the ice layer, a high-energy E-beam is then employed to pattern the ice layer at an E-beam dose that is at least two or three orders of magnitude greater than the dose employed for imaging the substrate surface through the ice layer, and can be 1000 times greater than the imaging dose. The ice layer pattern can be written, e.g., to define the location of metal deposition for forming electrical connections between the selected nanotube and the metal contact pads on the surface. The substrate including the nano-patterned ice resist layer is then transferred onto a metal deposition chamber of the EBIL cluster tool and a selected metal such as Pd is sputtered over the entire substrate surface. The substrate is then removed from the metal deposition chamber and, while still frozen, immediately immersed into a selected solvent, e.g., isopropanol, held at room temperature, whereupon the Pd film on top of the ice resist drifts away as the ice is melted from the substrate surface, in a lift-off process, leaving the pre-formed Mo leads connected to the SWCNT with Pd interconnections only where the ice had been removed by the E-beam.

Considering now specific control of parameters for condensation of an ice layer and for lift-off lithography employing the ice layer, the parameters of such ice layer formation and lift-off processes are described in U.S. Pat. No. 7,435,353, issued Oct. 14, 2008, and in U.S. Pat. No. 7,524,431, issued Apr. 28, 2009, the entirety of both of which are hereby fully incorporated by reference.

As explained therein, the originating source of vapor for producing a condensed ice layer can be one or more solid, liquid, vapor-phase gas, vapor, gas, or other constituents or a combination of constituents. All that is required is the delivery of a vapor to the process chamber for ice condensation on a structure in the chamber. For example, atomization, sublimation, or sputtering techniques, or other suitable solid, liquid, or vapor phase chemical processing can be employed for producing the vapor to be condensed. In an example process for producing a solid-condensed-gas layer from water vapor, a source of water vapor, e.g., liquid water, Epsom salts, sulfate, or other high vapor pressure solid that can vaporize, or other vapor source, is provided. The injector to the chamber can be provided as, e.g., a simple leak valve, a mass flow controller, or other suitable injector. It can be preferred to control introduction of the water vapor, and given that the injector may include a tube nozzle that produces directional vapor injection, a highly controllable valve or other controller can be preferred along with a diffuser or other device for enabling diffusivity of vapor introduction to the chamber.

It is found that the proximity of the vapor injector of the chamber to a structure in the chamber on which an ice layer is to be formed can impact the solid condensate formation. Specifically, it is found that shadowing and point source effects can occur for close injector proximities. It is therefore preferred that the scale of the structure be considered relative to the distance from the structure holder to the chamber injector. A relatively larger distance can be preferred for larger structure surfaces, with the injector and/or structure holder positioning adjusted accordingly. In addition or alternatively, parallel vapor sources, e.g., shower head arrangements, can be employed. For completely non-directional, conformal ice deposition, which can be especially desirable on a freely-suspended structure such as a nanotube suspended across a trench or aperture, both the vacuum conditions as well as the distance between the chamber injectors and the sample substrate can be adjusted such that the injector distance to the sample substrate is much larger than the mean-free-path of the incoming condensable vapor molecules. This can be done by raising the pressure in the vacuum chamber, either by introducing more condensable vapor or, more preferably, by introducing a mixture of inert gas molecules with the condensable vapor that is being introduced.

During ice layer formation, the temperature of the substrate or other structure on which ice is being formed is held below a temperature at which the water vapor condenses to form a solid ice condensate layer. For many applications, it can be preferred to maintain the structure temperature at 180 K or less, and more preferably to maintain the structure temperature at 130 K or less, e.g., about 110 K, to enable formation of an amorphous ice condensate layer. It is found that the characteristics of an amorphous, vitreous layer, are preferred for enabling optimal coverage of the surface features by a condensed ice layer, and for enabling precise control of local removal of the ice layer by the E-beam. It can be preferred to maintain the cold finger at a temperature that is less than that of the structure so the net flux of any vacuum contaminants is greater onto the cold finger rather than the structure.

For example, with a structure temperature set at less than about 130 K for condensation of the ice layer, a cold finger temperature of about 77 K, produced by liquid nitrogen cooling, can be preferred. The cold finger can be positioned quite close to the structure holder, and preferably is set as close as possible to the structure.

In addition to thermal control, there is required the control of the pressure of the vapor in the vicinity of the structure on which the ice layer is to be formed. The background pressure of the process chamber is not in general as important as the pressure local to the structure, which more closely dictates the solid condensate formation. Specifically, it is found that the local pressure directly impacts the solid condensate formation characteristics and rate. For example, it is found that a uniform, smooth, solid ice layer can be formed from water vapor when the condensate layer is produced at a rate less than about 25 nm/sec. Given a structure temperature less than about 180 K, and more preferably less than about 130 K, a local pressure that is less than about $10^{-4}$ T can be employed for achieving this solid condensate formation rate. But this slow ice condensation rate can also be achieved by higher pressures, if desired, e.g., to assure completely conformal deposition, by, e.g., mixing the incoming water vapor with a non-condensable molecule, such as argon. The resulting ice layer is stable and does not degrade. It is known that at a temperature of about 128 K, ice sublimes at a rate of only about 0.3 monolayers/hour with a sublimation energy of about 0.45 eV. As a result, so long as the temperature of the chamber is maintained at <130 K, the water ice layer is stable and will not significantly sublime or otherwise degrade.

Under the solid ice condensate formation conditions just given it has been found experimentally that the ice condensate is smooth and uniform, and appears to be amorphous at the resolution of a SEM image. With SEM monitoring of the ice condensate layer while the temperature of the silicon wafer was increased to about 153 K, it was experimentally found that the ice condensate surface image transitions from a smooth to a granular appearance. This granular transition corresponds to the amorphous-to-cubic ice phase transition temperature of ice, and indicates that maintenance of an ice condensate layer at temperatures below about 130 K can maintain a stable amorphous morphology. It is recognized in accordance with the invention that temperatures above 130 K can be employed where the morphology of the resulting solid ice condensate layer is acceptable.

Further, a solid ice condensate layer can be formed selectively at specific locations of a structure surface, e.g., by self-assembly processes. Specifically, conventional self-assembly processes can be employed to produce arrangements of layered regions on a substrate surface that are selectively hydrophobic or hydrophilic. With such an arrangement of hydrophobic and hydrophilic surface regions, condensation of water vapor can be carried out to form a solid ice condensate layer only on the hydrophilic surface regions.

EXAMPLE I

EBIL Fabrication Sequence for SWCNT FET Production

Molybdenum contact pads were provided on a silicon substrate having a blanket coating of a 500 nm-thick $SiO_2$ layer and a 60 nm-thick $Si_3N_4$ layer. The substrate was etched with KOH to form a trench and ion beam milling was employed to form a slit in the trench. Iron catalyst pads for synthesis of single wall carbon nanotubes (SWCNTs) were patterned to lay near the focused ion beam-milled slits such that the SWCNTs would grow across the slits. Standard E-beam lithography and lift-off was carried out to overlap the catalyst pads with the preformed Mo pads, which could be held at ground potential. This geometry produced ideal conditions for imaging the SWCNTs by transmission electron microscopy.

After SWCNT growth, the sample was loaded into the SEM of the EBIL cluster tool of FIG. 2 via a door on the metal deposition chamber that served as a load lock which could be isolated from the main chamber with a butterfly valve. The specific design and mechanical details of the IL cluster tool are provided below. After evacuating the metal deposition chamber, the sample was moved onto the SEM's cryo-stage and cooled down to ~110 K. Base pressure in the SEM was <0.8×10$^{-4}$ Pa. A large cold finger held at ~80 K maintained the partial pressure of water to <3×10$^{-6}$ Pa as measured by a residual gas analyzer. Sample loading, cooling and stage thermal stabilization required about one hour. Water vapor from a hydrated salt ($MgSO_4 \cdot 7H_2O$) was leaked into the SEM through a nozzle just above the sample and condensed as amorphous ice on the cold sample. The ice thickness was determined by patterning wells into the ice and measuring their height projection by tilting the sample. About 80 nm of ice was deposited in 30 s. The ice deposited even around free-standing SWCNTs. After ten minutes of beam conditioning the SWCNTs positions were mapped through the ice layer using a 20 pA beam at 2-4 kV. This exposed the ice to an E-beam dose of about 10$^{-4}$ C/cm$^2$. With this mapping, there was determined a particular SWCNT for which electrical contact was selected.

An intense E-beam of 15 kV or 30 kV and 1-2 nA was then used to remove the ice in a pattern that formed a mask for metal deposition in the process of producing electrodes for contacting the selected SWCNT. A dose test determined the required number of electrons to remove sufficient ice to expose the underlying substrate, and was 1 C/cm$^2$ at 15 kV. Dose testing, computer assisted design of electrodes, alignment, and ice resist patterning required about one hour. After the ice resist patterning, the sample with a nano-patterned ice resist layer was transferred onto the metal deposition chamber cryostage of the EBIL cluster tool, and held at 165 K, where ~5 nm of ice was allowed to sublime off the entire sample before metal deposition.

Metal layers, of 1 nm-thick Cr and 10-20 nm-thick Pd, were sputtered over the entire sample. Before sputtering, the base pressure in the metal deposition chamber was 3×10$^{-6}$ Pa. During Pd sputtering, at a rate of 1 Å/s, the Ar processing gas pressure was maintained at 0.7 Pa. The sample was removed from the metal deposition chamber while still frozen and immediately immersed into an isopropanol bath held at room temperature, whereupon the Pd film on top of the rapidly melting ice resist drifted away, leaving the pre-formed Mo pads connected to the SWCNT by the Pd metal only at locations where the ice layer had previously been removed by the E-beam. The Pd deposition and lift-off step took about one hour, resulting in a total process time of about three hours.

Two methods were used to evaluate E-beam-induced defects or contaminants on the finished device. First, tapping mode AFM was used to inspect and compare SWCNT-metal nanostructures made by the EBIL method compared with those produced with conventional E-beam lithography employing a PMMA resist. It was determined that following the EBIL process, the root-mean-square surface roughness of the device surfaces barely increased, changing from an initial value of 0.25-0.27 nm to a value of 0.31 nm. This small increase in surface roughness with the EBIL process contrasts with a much greater increase, to 0.81 nm, that was measured for the sample on which conventional PMMA resist was employed.

The ability of free-standing SWCNTs to nucleate the growth of $Al_2O_3$ during atomic layer deposition (ALD) of $Al_2O_3$ on the entire sample was also investigated. Pristine, defect-free SWCNTs do not nucleate the growth of $Al_2O_3$, whereas contaminants or SEM-induced damage sites do allow for nucleation of $Al_2O_3$ on SWCNTs. ALD of $Al_2O_3$ was carried out in an in-house designed system using 100 cycles to grow ~11 nm-thick $Al_2O_3$ with trimethyl aluminum and water as reagents on the SWCNTs after the EBIL process. The reactor temperature was set at 240° C., and purge pressure was set to 100 mTorr.

The ALD process confirmed that the free-standing, unprotected SWCNTs imaged by SEM did nucleate $Al_2O_3$ growth, while those that had been imaged through an ice layer in the IL process did not accommodate $Al_2O_3$ nucleation. This demonstrates that the EBIL process produces devices that remain free of processing residues and E-beam-induced defects that are produced by conventional lithographic and imaging steps and that alter the electrochemical properties of SWCNTs from their natural state.

Electrical measurements under ambient room temperature conditions showed that the SWCNTs having electrical contacts formed by the EBIL process contained both semiconducting and metallic tubes at a ratio of 2:1, as commonly observed for CVD grown tubes. FIG. 3A is a plot of measured conductance for a metallic SWCNT FET and a semi-conducting SWCNT FET, both produced by the process just given. FIG. 3B illustrates the measurement set-up.

Keeping the source-drain voltage over the SWCNT constant at 10 mV, the gate voltage was swept at 5 V/min from −10 to 10 V and back from 10 to −10 V. Arrows indicate the sweep direction. The dotted lines provide the measured data for a 60 kΩ metallic tube after annealing at 300° C. The solid lines provide the measured data for a semiconducting tube after annealing at 600° C. The ON resistance was measured as 380 kΩ. While sweeping the back-gate bias from −10 V to 10 V, the semiconducting tube switched to its ON state at a negative gate bias, indicating hole conduction, while the metallic tube did not show a significant back gate response. The hysteresis commonly observed in ambient conditions for SWCNT FETs fabricated with conventional photoresist is noted.

Because metal films deposited onto cold surfaces tend to be nanoporous, there was investigated the electrical quality of the metal contacts and leads formed by the EBIL process. EBIL-fabricated devices were compared with conventionally-fabricated SWCNT devices on $SiO_2$-coated Si substrates. Each 10-nm-thick source and drain Pd electrode covered a 0.8 μm-long segment of the SWCNT, with a 2 μm spacing between the two electrodes. The EBIL SWCNT FET source-drain resistances, Rsd, ranged between 0.33 MΩ and 16 MΩ. The source-drain resistances, Rsd, of SWCNT FET devices that were formed employing conventional photoresist in E-beam processing were measured to be ~50 kΩ. The source-drain resistance of the EBIL devices was reduced by annealing in an Ar atmosphere at a temperature between about 300° C. to 600° C. This annealing step reduced the EBIL-fabricated FET Rsd by more than ten-fold and yielded contacts having source-drain resistance, Rsd, were comparable to those obtained for the SWCNT FETS produced using standard resist-based E-beam lithography: metallic SWCNT FET devices with Rsd between 60 and 90 kΩ and semiconducting SWCNT FET devices with Rsd down to 100 kΩ. The improved contact resistance is a result of high temperature densification of the cold-deposited Pd contacts.

Based on this data, it can be preferred to anneal metal layers that are deposited by the EBIL process if it is desired to reduce contact resistance. Annealing can be carried out, e.g., in a tube furnace, in Ar gas. At an annealing temperature above about 300° C., it can be preferred to coat a Si substrate with a nitride layer, such as $Si_3N_4$, rather than $SiO_2$. It further can be preferred to deposit a 1-nm-thick Cr adhesion layer before deposition of a Pd layer. It is understood that Pd diffuses into $SiO_2$ at temperatures above 300° C. and therefore can cause a short circuit between a silicon substrate and source drain electrodes that are disposed on the oxide surface layer. Substitution of a $Si_3N_4$ surface layer for the oxide surface layer inhibits such diffusion. Furthermore, a Pd layer can de-wet and forms islands when annealed above 300° C. The inclusion of a lower Cr layer improves Pd adhesion and inhibits such island formation and the associated metal contact discontinuities. It is therefore understood that for applications in which contact resistance is to be lowered by a final annealing step, it can be preferred to employ a Pd—Cr metal combination and to employ a nitride, rather than an oxide, substrate surface layer.

The experimental results described above demonstrate that the EBIL methodology solves several problems often faced in designing and producing nano-devices. Ice-lithography is a simpler process than standard E-beam lithography. State-of-the-art E-beam photoresist processes involve mapping of a sample surface prior to photoresist deposition, often with a time-consuming AFM-based process, spinning an organic photoresist on the sample, baking the resist to remove solvents, exposing the resist in a selected pattern with the E-beam, chemically developing the resist, and forming or depositing structures, such as contacts, in the resist patterns, and cleaning or scrubbing to remove the resist.

In an E-beam imaging and ice-lithography process as provided herein, an ice layer is vapor-deposited, the sample surface is fully protected while E-beam mapping of the surface is conducted through the ice layer with minimal ice layer removal, no baking step is required, the same ice layer that was employed as a protective layer for mapping is employed as a pattern layer that is directly removed by E-beam exposure and thus no development step or cleaning/scrubbing step is required. These benefits are amplified by the ability to protect a substrate surface with the same material layer that is employed as the layer that is to be patterned. The simpler process and the protective effect of the ice enable a dual imaging-lithography process that can be conducted in a cluster tool rather than in different machines.

EXAMPLE II

EBIL Fabrication Sequence for Three-Dimensional Structures

Photoresist spinning works very well for flat substrates and chips that are generally larger than about 3 mm×3 mm. Photoresist spinning does not, however, uniformly cover micro-scale, 3-D micromachined structures, such as probes for scanning probe microscopy. Vapor-deposited ice provided in the EBIL process sequence can be employed to cover 3-D structures easily. For example, as shown schematically in FIG. 4, the EBIL process enables production of a metallic coil on an AFM cantilever.

In this process, the following steps are conducted: an ice layer is condensed on the cantilever, E-beam mapping of the cantilever determines the coordinates for patterning of the ice layer, the layer is patterned by the E-beam, metal is deposited over the ice layer and the cantilever, and the ice layer and metal are lifted off, resulting in the metal remaining on the cantilever only at the locations corresponding to the ice layer pattern openings. It would be extremely difficult to make such a coil on an AFM cantilever using standard spin-coating, which is limited by, among other factors, the "edge-bead" of the resist, which can occupy the entire area of the cantilever.

This example demonstrates that the EBIL process can be employed to lithographically pattern layers on any three-dimensional structure, including suspended and overhanging structures, such as MEMs cantilevers in general. MEMs and nano-scale cantilevers with added metal structures are important for, e.g., the study of fundamental quantum mechanical systems, such as Bose-Einstein condensates and mesoscopic persistent currents. Many sensor and actuator applications rely on metal structures for sensing and/or actuation. The EBIL process enables lift-off processing to form whatever metal structure is desired on a MEMs structure such as a commercial silicon micro-cantilever. As explained above, for imaging of the structure through a protective ice layer, and for forming electrically isolated conducting patterns on the structure, it can be preferred to electrically insulate the structure with, e.g., an oxide or a nitride surface coating.

As a further example of such three-dimensional patterning, there can be lithographically processed the pyramidal tip of an AFM cantilever by the EBIL sequence herein. FIG. 5 schematically illustrates the resulting structure of a Ti/Au rectangular region coated with metal on the very tip of an AFM pyramid located at the edge of an AFM cantilever.

In one experimental example of such, an AFM cantilever was loaded onto the cryo-stage of an EBIL tool and cooled to ~120 K. Water vapor was introduced into the vacuum chamber and deposited ballistically onto the cold sample as in FIG. 1A. The average thickness of the ice on the AFM pyramidal inclined surfaces, ti, is given by $$t_i = \frac{A_p}{A_i} t_p,$$

where Ai is the surface area of the pyramid, $A_p$ is the projected area, and $t_p$ is the ice-thickness on surfaces parallel to the cryo-stage. After mapping the AFM pyramid spatial coordinates through the ice at low E-beam dose as in FIG. 1B, the focused E-beam was used to remove the ice at the pyramid tip and expose the underlying pyramid through a square opening in the ice layer as in FIG. 1C. Ti and Au were then deposited over the entire AFM cantilever and pyramid, as in FIG. 1D, and then the cantilever was immersed into isopropanol held at room temperature as in FIG. 1E. As the ice melted, metal remained adherent only on the tip of the pyramid where the ice had been patterned. It was found that this EBIL process enabled clean lift-off with no undesired metal flakes This EBIL patterning of an AFM tip has many applications. For example, a method of studying the binding forces between two biomolecules involves coating an AFM tip with gold and immobilizing biomolecules on the probe using sulfur chemistry. Nanopatterning of gold on the probe would allow precise control over the location and quantity of immobilized biomolecules. Other applications of patterned AFM tips include tip-enhanced Raman spectroscopy for chemical analysis and nano-plasmonics, magnetic force microscopy, scanning single-electron transistor microscopy for studying mesoscopic systems, and other AFM related fields.

In a further example of such micro-scale and nano-scale three-dimensional patterning, both sides of a fragile $Si_2N_3$ membrane can be patterned with the EBIL process herein. Such a membrane can be important for, e.g., transmission electron microscope grid manufacture. As an example, the EBIL process enables the formation of metallic structures less than 10 nm wide and spaced apart with gaps less than 7 nm on a free-standing membrane. Each side of the membrane can be coated with an ice layer, imaged, and patterned to provide metallic structures on the membrane surface. Note that in the EBIL process the metal lift-off step is found to be very clean with no undesired metal flakes observable in spite of the fact that the fragile $Si_2N_3$ membranes do not tolerate the common ultrasonication used to assist lift-off when using polymeric resists. Even the back side of such membranes, with 200-µm-deep concavities on which unusable resists would form using spin coating can be readily patterned with the EBIL process.

EXAMPLE III

EBIL Patterning of and Metal Deposition on Carbon Nanotubes

For many sensing and analysis applications, it is commonly preferred to dispose a carbon nanotube, such as a SWCNT as a freely suspended structure across, e.g., an aperture or trench. Such freely suspended SWCNTs are incompatible with conventional spin-coated resists not only because they are non-planar, but also because they are very fragile. With the EBIL process herein, there was fabricated electrically insulating nanoparticles coaxially surrounding titanium on a freely-suspended SWCNT.

SWCNTs were synthesized across a 1-µm-wide aperture in a silicon nitride membrane. The nanotubes were then coated with ice in the EBIL vacuum chamber, as in FIG. 1A. The ice-covered nanotubes were then imaged in the SEM, as in FIG. 1B, at a low E-beam dose that did not remove a significant amount of ice. Then nominally 25-nm-wide ice-free regions were patterned across the ice-coated SWCNTs to remove the ice at pattern sites. In this pattern, the vertical lines written by the E-beam were separated by 150 nm. After writing, the samples were coated with 5 Å of Ti, which has been shown to form continuous and uniform coatings on nanotubes. To avoid violent interfacial forces, the samples were dried by carbon dioxide critical point drying after they had been immersed in isopropanol to lift off the metal.

Subsequently, the SWCNTs were loaded into an atomic layer deposition chamber (ALD). ALD does not grow on pristine SWCNTs as explained above, but will grow on oxides. Upon exposure to air, the patterned Ti layer on the SWCNTs formed an oxide, and therefore served as the nucleation sites for ALD growth. As a result, $Al_2O_3$ nanoparticles were formed on the SWCNTs at locations precisely defined by the E-beam lithography The SWCNTs were then again imaged in the E-beam. It was found that the nanoparticles are small enough to be electron transparent, so that the SWCNTs are clearly visible even where they are coaxially coated by the $Al_2O_3$. The geometry of the nanoparticles was clearly determined by the ice lithography and ALD processing parameters.

This example demonstrates that the EBIL process can be used to fabricate metal-semiconductor junctions on CNT scaffolds, CNT-based plasmonic devices, and metal-coated CNT tips for AFM. Moreover, the EBIL method can be used to pattern metal or insulator nanostructures on other types of suspended materials like nanowires of single layer graphene.

EXAMPLE IV

EBIL Cluster Tool Processing

An experimental EBIL cluster tool having the configuration of the tool in FIG. 2 was constructed. In general, the architecture of an EBIL cluster tool can be divided into two or more major structures, namely, the SEM chamber and one or more processing chambers. In the experimental tool, a two-part cluster tool was provided with an SEM chamber and a metal deposition chamber, which also functions as a load lock for sample exchange. The function of the SEM part is cooling the sample down to temperatures that allow growth of water ice layers, introduction of water vapor over the sample, imaging and mapping of a sample through an ice layer, and selective ice removal for ice layer patterning by the E-beam. A material such as a metal is deposited in the metal deposition chamber.

In the experimental EBIL cluster tool there were provided a combination of features, some of which are commercially-available components whereas others were in-house-designed instruments. In the experimental EBIL cluster, vacuum components and feed-through were selected by availability from the following suppliers: Kurt Lesker, PA, Metal Deposition Chamber Vacuum, CA, Insulator Seal, FL, and VAT INC, MA. Temperature control and monitoring was implemented with in-house-built electronics with six independent temperature controllers (CN77000 series, Omega Engineering, CT, USA). K-type thermocouple sensors were employed for all temperature measurements.

An SEM, e.g., a JEOL 7001F SEM (JEOL, MA, USA) served as the base of the EBIL cluster tool. This SEM has a thermal field emission E-beam gun that gives a very stable and high beam current. The sub-5 nm resolution achievable at 1 nA of beam current is important for ice lithography given that the number of electrons required to remove an ice layer of about 100 nm in thickness, also called the clearance dose, is about 10000 times higher than that required for a standard E-beam PMMA resist. Cold cathode field emission systems are less suited for ice lithography, due to smaller beam currents. The JEOL 7001F has many instrument ports, which are of particular use for the EBIL cluster tool. A liquid nitrogen ($LN_2$) cryo-trap was mounted above the diffusion pump to condense volatile gasses and improve the SEM chamber cleanliness. For monitoring gasses in the vacuum system and leak checking operations, a residual gas analyzer was installed (RGA200, Stanford Research Systems, CA, USA).

The first step of the EBIL process is sample cooling, which can take place inside the SEM chamber of the tool or in another chamber, e.g., a metal deposition chamber, which in the example tool also serves as the load-lock through which a sample is introduced into the SEM. To implement this feature, the cryo-stage was designed with a connection via a flexible oxygen free copper braid to an in-house-designed heat transfer rod that was immersed in a liquid nitrogen bath. The cryo-stage was mounted onto the SEM high precision stage. The flexible copper braid design allows the cryo-stage to move freely. No particular cryo-stage is required as long as it can attain and maintain the temperature needed for water ice imaging and lithography. For automation of an EBIL process, e.g., it can be preferred to employ a relatively large cryo-stage mounted on, e.g., a high-precision stage that is characterized by a precision of less than 1 nm. Originating from the SEM gun, the E-beam for imaging through an ice layer and pattern writing of an ice layer passes through the SEM objective lens and an aperture in the cold finger that was made from an oxygen-free copper plate connected to a $LN_2$ reservoir.

Held at a selected temperature, e.g., 83 K, the cold finger, having a width twice as large as the sample holder, protects the sample from contamination in the SEM vacuum. It can be preferred to include a number of well-located cold traps with sufficient surface area to reduce condensation of vacuum contaminant molecules on a sample. In one example, a cold finger is fixed to a $LN_2$ dewar made of two concentric stainless steel tubes. The inner tube contains the $LN_2$, and the space between the tubes share the SEM chamber vacuum. Typically, for ice layer growth, structural imaging and mapping, and E-beam patterning, the distance between the SEM objective lens and the sample is preferably about 10 mm. For reducing contamination and reducing residual water in the system, it can be preferred to employ a relatively powerful vacuum pump to achieve superior vacuum conditions.

In the experimental EBIL tool, the SEM cryo-stage was composed of an inner body made from gold-plated copper that was soldered to the cooling braid, and thermally insulated from an outer jacket made from bronze. The outer jacket is in thermal contact with the SEM stage. The inner body and outer jacket were mechanically connected with minimal thermal connection by employing via two threaded Vespel pins and one spring-loaded stainless steel pin plunger, but a number of alternate designs with minimal thermal connection are possible.

In operation, as the cryo-stage is cooled down to a selected ice layer formation temperature, e.g., 110 K, then due to the difference in thermal expansion coefficients, the pin plunger is required to secure the mechanical stability of the three contact points between the jacket and the cryo-stage body. To ensure a good thermal contact between the sample holder and the cryo-stage body, four adjustable spring loaded ball plungers in the stainless steel dove tail mechanically secured the sample holder.

In the experimental EBIL tool, to enable in situ electrical measurements of nanodevices there were provided sample holders with four male electrical connectors. Low-melting point solder was used for attaching the copper braid to the cryo-stage body to avoid oxidation of the copper braid, which could compromise heat conductivity. To allow experiments above 110 K, a low magnetic field heater cartridge (Sun Electric Heater, MA, USA) coated with heat conducting grease was fitted into the cryo-stage body. The use of a heater could cause increased boiling of $LN_2$ cooling the cryostage, and therefore it is preferred to vibrationally insulate the $LN_2$ container from the microscope, since any vibration will deteriorate E-beam imaging and patterning.

This challenge was overcome by designing a heat transfer copper rod that was silver-soldered concentrically inside a stainless steel vacuum jacket protruding from the SEM in an L shape. One end of the rod was mechanically clamped to the braid and the other end of the copper rod that is exposed to atmosphere can be immersed into a $LN_2$ dewar sitting on the floor.

Vibrations from the boiling of $LN_2$ do not affect SEM imaging with this arrangement. If the copper rod is an integral part of a $LN_2$ dewar mechanically fixed onto the SEM chassis, it is found that the vibrations from the boiling $LN_2$ can make it impossible to carry out high resolution work. To reduce irradiative heating the copper rod and braid was wrapped in aluminized Mylar foil (ROL-VAC, CT, USA).

In the SEM chamber of the EBIL cluster tool, it is preferred that the partial pressure of water be relatively low, such that during a typical thirty minute E-beam writing duration, undesired background ice growth on the structure is negligible. The effectiveness of the cold finger and cryo-trap is therefore important. It was found that the cold finger cooled down from room temperature to 83 K within 30 min. Once refilled after reaching 83 K, the cold finger dewar contained sufficient $LN_2$ for more than 8 hours of operation. The liquid nitrogen cryo-trap contains sufficient $LN_2$ nitrogen for more than 12 hours of operation and the 5 L dewar for SEM cryostage keeps the stage cold for more than 48 h. During continual operation of the nitrogen cryo-trap, the overall vacuum improves slightly from $10 \times 10^{-5}$ to $7 \times .10^{-5}$ Pa, but the partial pressure of water in the SEM chamber decreases more than tenfold to below $10^{-6}$ Pa, which will cause less than 20 monolayers of water molecules to grow on an exposed cryogenic surface in 30 min. Because the cold finger is situated no more than 5 mm away from the sample, such that the local water partial pressure of water is much less than $10^6$ Pa, it is estimated that the background ice growth will be less than 5 monolayers in 30 min.

For superior ice lithography, growth of amorphous or vitreous ice is preferred, as explained above. At $10^{-5}$ Pa the transition between amorphous ice growth and crystalline ice growth is about 135 K. Therefore the cryo-stage preferably can reach temperatures well below 130 K. The experimental EBIL cryo-stage cools down from room temperature to 120 K within three hours and stabilizes at 108 K after four hours. The ratio of the thermal mass of the cryo-stage and the sample holder is about 3, and it is sufficiently large such that when a sample held at room temperature is transferred onto the cryo-stage held at 108 K, the cryo-stage temperature decreases to below 130 K within about 15 min. A short cooling time is preferred because prolonged cooling can increase deposition of contaminants on the sample.

The cryo-stage temperature control also has strict requirements for high-resolution SEM imaging. Any magnetic fields larger than about 0.3 mGauss can interfere with the E-beam, causing distortions in the SEM image as well as writing at high magnification. Due to thermal expansion, any temperature fluctuations will cause the sample to drift. Large magnetic fields, drift and finally vibrations from boiling $LN_2$ will strongly affect the E-beam writing. As detailed above, a heat transfer rod design can be employed to avoid vibrations from boiling $LN_2$ to be transferred to the SEM, such that high resolution imaging is possible when the stage temperature is stabilized at temperatures <130 K. Elevated stage temperatures are controlled by balancing heating by a low magnetic field heater cartridge and the constant cooling by $LN_2$. The heater is controlled by a feedback temperature controller that reads the stage temperature and sends out an output signal between 0 V and 10 V which is then fed into a low noise DC power supply (Agilent E3617A, MA, USA) sending 0 to 1 A through the heater. Testing the cryo-stage heating system, the stage temperature stability is better than 1 K such that temperature drift does not affect high resolution work. For high resolution work at low acceleration voltages below 5 kV, where the E-beam is most sensitive to magnetic fields, a constant current is preferably applied.

The water source, used for growing ice layers, can be, e.g., a hydrate salt such as $MgSO_4.7H_2O$, Such can be stored in a Pyrex or quartz tube that is mounted onto a valve manifold outside the SEM vacuum chamber. When mounting the water source, the tube also contains ambient air, which has to be removed from the water source. To make this possible, in the experimental EBIL tool the valve manifold consisted of a small vacuum chamber that can be evacuated through the metal deposition chamber, a pressure gauge tube (275 Convectron Gauges, Granville-Phillips, MA, USA), a valve to the water source, a valve to the metal deposition chamber and an ultra high vacuum variable leak valve (Varian, MA, USA) that controls the water vapor flow into the SEM chamber. Hydrate salt is preferred over liquid water as a vapor source because liquid water can occasionally condense into the leak valve, rendering the ability to control water flow for reproducible ice layer deposition impossible. The water vapor flow can be controlled in any suitable manner for a given application. A shower head can be employed for water vapor introduction to uniformly cover a large sample with ice, or an alternative vapor injection system can be employed. No particular vapor injection and flow control is required.

To form an amorphous ice layer, condensation of the ice can be conducted at a temperature less than about 130 K, e.g., about 123 K. In one example process with the experimental EBIL cluster tool, after purging the water source of air and any other contaminating gasses, between 900 and 1000 Pa of water vapor pressure was built up by allowing hydrated salt to degas, and then opening the calibrated leak valve to allow 6 nm/s of water ice to condense on the sample.

The thickness of the ice during ice condensation was determined by E-beam patterning of 800 nm-wide lines into the ice and down to the substrate, then subliming the ice at 163 K, and measuring the increase of the width of the 800 nm lines just before all ice is sublimed. Sampling the ice thickness over an area of 6 mm by 6 mm with 4 measurements at each corner and one in the center, the uniformity of ice thickness was found to vary by 14% (coefficient of variation).

For patterning of a condensed water ice layer, the EBIL tool can be fitted as-needed. For example, in the experimental EBIL tool, there was implemented a beam blanker (Deben, Suffolk, UK) and a SEM lithography system (NPGS 9, Nabity, Mont., USA) including software and a 16 bit pattern generator. This system enables control of the E-beam such that complex patterns can be formed in an ice layer, and enables alignment of patterns with other visible structures on a sample. For example, in the production of SWCNT FET devices, the imaging and control implementation enables alignment of metal patterns with Cr/Mo leads. It is recognized that in E-beam patterning, stray magnetic fields can deflect the E-beam by Lorentz force, possibly causing visible shifts in the SEM image and E-beam writing. To reduce stray magnetic fields down to 0.3 mGauss, an active magnetic field cancellation system (MK 4 EMI Cancellation System, IDE, MA, USA) was installed in the experimental EBIL tool.

If desired, there can be included in the EBIL cluster tool pattern recognition software such that images obtained of a sample through an ice layer can be employed for automatically generating patterns to be imposed on the ice layer. In addition, after each ice layer patterning step, additional images can be employed for automatically generating further or adjusted patterns.

Once patterning of the ice layer is complete, the sample is transferred within the EBIL cluster tool to a second processing chamber. In the experimental EBIL tool described here, the second chamber is provided as a metal deposition chamber, as shown in FIG. 2.

To support the weight of the metal deposition chamber in the experimental tool, the chamber was mounted with a supporting steel frame structure to the side of the microscope. For a good metal deposition the base pressure of the chamber vacuum should be below $10^{-4}$ Pa. This can be achieved with a large 6 inch-diameter low-vibration water-cooled turbo molecular pump (HiPace 300 from Pfeiffer Vacuum, Asslar, Germany) backed by a rotary pump (Pascal 2010 from Adixen, MA, USA). But the large turbo molecular pump (TMP) is characterized by such a large mass that to keep the overall metal deposition chamber mass low, no vibration insulation or flow regulation valve was mounted between the TMP, which is the standard configuration for high vacuum metal deposition chambers. It can be preferred to include such vibration insulation and flow regulation equipment. While vibrations from the TMP can strongly affect the E-beam writing, the TMP vibration levels are sufficient low such that it was required to switch it off only if patterns of less than 100 nm wide were formed. Vibration from the rotary pump can be minimized by using a combination of heavy thick-walled tubing (Tygon series from McMaster, Mass., USA) and vibration isolation unit (JEOL, MA, USA).

In the experimental EBIL cluster tool, the vibration isolation unit also contained a molecular sieve that restricts backflow of mechanical pump oil from the rotary pump to the metal deposition chamber. The metal deposition chamber pressure is monitored by a gauge tube and thermal ion gauge (Granville-Phillips, MA, USA). To protect the SEM vacuum, a logic circuit can be included to control the pneumatically actuated gate valve (VAT, MA, USA) separating the metal deposition chamber and SEM vacuum chamber. A differentially-evacuated high vacuum linear-rotary transfer rod (Thermionics, CA, USA) can be used for sample transfer between the SEM and metal deposition chamber.

For many applications, such as SWCNT FET and other nanodevice fabrication applications, a stack of two different metals are often required. For example, a thin layer of Cr or Ti can be necessary for improved adhesion to non-metal materials. The EBIL cluster tool can be designed to deposit two or more different metals and other materials, in contrast with commercial cryogenic systems for biological applications. In the experimental tool, the two sputtering guns (1.3" MAK, MeiVac, Ca, USA) were disposed to form a 60° angle with the plane of the metal deposition chamber cryo-stage. The sputter gun controller was implemented as the MDX 500 from Advanced Energy, Co, USA. To avoid undesired water introduction into the metal deposition chamber, the high purity processing gas Ar was leaked into the metal deposition chamber via a high vacuum line through an ultra high vacuum leak valve.

A quartz crystal thin-film thickness monitor (STM-2XM, Sycon Instruments, NY, USA) that measures the thickness of metal sputtered onto the sample, and a shutter for accurate control of metal deposition, were installed on the same flange in the experimental EBIL tool. A vespel piece thermally insulated the cryo-stage from the metal deposition chamber. Similar to the SEM cryo-stage, the metal deposition chamber cryo-stage also included a heater cartridge, and the sample holder was kept in thermal contact with the stage via a dovetail with the spring loaded ball plunger design.

While the SEM cryo-stage is constantly in vacuum, because the metal deposition chamber is subjected to frequent venting to atmosphere, the metal deposition chamber cryo-stage design has to allow rapid heating to avoid frosting when venting. In addition, rapid cooling is required to shorten the total process time. The vibration requirements are less strict for the metal deposition chamber cryo-stage and the stage remains stationary. For rapid heating or cooling the metal deposition chamber cryo-stage temperature is controlled by either flowing compressed air or $LN_2$ through a copper tube soldered to the stage. The temperature is regulated by controlling the flow of $LN_2$ or air by a circuit of manual valves and an automatic solenoid valve. In the experimental EBIL tool, on the inlet side, the circuit was connected to a 160 L $LN_2$ dewar and compressed air which flow can be individually regulated by two manual valves. The flow of gas is carried into the heat transfer copper tubing inside metal deposition chamber via thermally insulated (Armaflex, Homan Associates, MA, US) stainless tubing.

In the experimental EBIL tool, on the out-let side, the gas is able to leave the circuit via three different exits, namely, a pressure relief valve that prevents pressure build up above 1.5 bar, a $LN_2$ compatible manual valve (Diaphragm-Sealed, Swagelok, Mass., USA), and a solenoid valve (Gems Sensors & Controls, CT, USA). The cryo-stage is cooled down by flow of $LN_2$ through the circuit. Under normal cooling operations, the inlet manual valve is open and the out-let manual valve is closed. The temperature controller unit senses the cryo-stage temperature and controls it by opening and closing of the solenoid valve. To heat the cryo-stage quickly, $LN_2$ flow is stopped at the 160 L dewar, and compressed air is flowed through the circuit. With this design, the cooling time for the metal deposition chamber cryo-system is less than 10 min and the heating the system to room temperature from cryogenic temperatures is about 20 min.

To keep the metal deposition chamber free from water vapor and vacuum contamination, which will deposit on a cooled sample in an uncontrolled fashion, a cold finger, cooled to 103 K by an independent liquid nitrogen/compressed air line, was installed between the metal deposition chamber cryo-stage and the shutter. The metal deposition chamber cold finger temperature can be controlled by an identical circuit as the metal deposition chamber cryo-stage.

To avoid any undesired growth of ice during transfer of a sample between the EBIL cluster chambers, the sample is preferably transferred from the SEM cryo-stage to the metal deposition chamber cryo-stage without breaking the vacuum. In case even a very small amount of ice is deposited on the patterned sample during the transfer, it can be preferred to maintain the metal deposition chamber cryo-stage at a selected temperature, e.g., 166 K, at which the ice sublimes does sublime, e.g., at a rate of about 10 nm/min after thermal equilibration. For smaller features, this process is preferably carried out at lower temperatures, for which the sublimation rate is less than about 1 nm/min. During metal deposition, Ar is used as the standard processing gas. The plasma can be ignited at 1.3 Pa, and to achieve a Pd deposition rate in the range of 2 Å/s, the deposition pressure is set to 0.67 Pa (5 mTorr) by adjusting the Ar gas flow. After metal deposition, the metal deposition chamber is vented to atmosphere using dry nitrogen.

At the end of the metal deposition process, the sample can be removed from the cluster tool by unloading the sample holder from the metal deposition chamber cryo-stage to the ambient. If further processing is to be conducted, such can then take place. For example, for the SWCNT metal lift-off process described above, the sample can be removed from the metal deposition chamber and plunged into isopropanol held at room temperature, to conclude the ice lithography process. The cryo-stage and cold finger is then heated to room temperature and ready for a new sample and ice lithography process.

With this experimental EBIL cluster tool configuration, E-beam patterning of a 30 nm-thick condensed ice layer was conducted. At an E-beam energy of 15 kV and 100 pA of E-beam current, and with a 1 $C/cm^2$ dose, the finest lines that could be patterned in the ice layer were <10 nm wide. It was determined that the area dose required to remove 80 nm of ice at respectively E-beam energies of 30 kV, 15 kV, and 5 kV were 0.5 $C/cm^2$, 0.9 $C/cm^2$ and 1.0 $C/cm^2$, respectively. It was observed that during E-beam patterning of an ice layer, ice re-deposition could occur at a site after ice removal at that site, whereby the last location of patterning well-defined but the first site of patterning can be smeared out. Such redeposition is a well-known phenomenon in other removal process such as ion-beam milling and ion sculpting. To remove re-deposited ice, it can be preferred to sweep the E-beam several times.

As explained previously, it can be preferred to customize one or more elements in the EBIL cluster tool to obtain superior performance for a desired application. In the SEM chamber, exchanging the diffusion pump with a more powerful TMP option can improve the SEM vacuum such that undesired contamination and water are reduced. The smallest features are created at low working distance. But it may not always be possible to work at low working distance, e.g., if the SEM imaging sensor (Everhart-Thornley detector) is screened by the SEM cold finger; similarly, imaging at short working distances may not be possible. By installing an electron detector option inside the pole piece (in-lens detector), work at low working distances can be accomplished.

In the metal deposition chamber, there are many considerations for customization. For ambient sputtering processes, metal atoms have sufficient energy to diffuse on a sample surface to form a uniform coating such that the direction of the deposition is not critical. But when a metal is deposited at cryogenic temperatures, the film growth is highly ballistic, such that no surface diffusion takes place. Ballistic deposition is highly directional, such that if a thin film is deposited at an angle that is not perpendicular to the surface, a very porous film can be formed. Also, the angle of the metal source can be important; the angle between the metal source and the sample surface is 60 degrees in the experimental tool, such that a 100-nm-thick ice layer will create a shadow that is up to 58 nm-wide on the surface. Therefore, to avoid shadows and porous film formation, it is preferred that the angle between the metal source and the sample surface be 90 degrees.

During the sample transfer process between chambers, the partial water vapor pressure was found to increase by $4 \times 10^{-5}$ Pa, due to the inherent leaking O-ring design of the differentially-pumped sample transfer feed-through. A magnetic transfer system can be employed to eliminate this leak, which causes an undesired growth of about three layers of solid water molecules on the sample during the 10 s of transfer time. Adding vibration insulation to the TMP and a flow regulating valve can also allow much cleaner sample transfer and metal deposition.

In general, the EBIL cluster tool can be adapted for conducting any number of suitable ice layer-based processes. All that is required is the ability to maintain a sample temperature below the sublimation temperature of ice layers on the sample, and a mechanism to maintain a sufficient vacuum free of condensable vapors. For example, to add material to a sample, there can be included a chamber for sputtering that is DC or RF magnetron-assisted. The metal deposition chamber described above employs a DC magnetron sputtering system, in which Ar ions in a plasma bombard a metal target, and the ejected atoms deposit onto the sample. But due to charging effects, insulators must be sputtered using a radio frequency (RF) sputtering system. Any suitable sputtering system can be employed.

In addition, there can be included chambers for thermal, E-beam, or other suitable evaporation method. Metals and insulators can also be ejected from a target by evaporation. Here a target can be heated to evaporation temperatures by an energetic electron beam or by passing a high electrical current through the material. While the metal or insulator targets to be evaporated onto a sample must, of course, be heated to evaporation temperatures, the sample that is partially under an ice layer must be kept cool by distancing it away from the hot target. Chambers for material deposition by laser ablation or sputtering can further be included, in which, e.g. an Excimer laser is provided to heat up a target very locally. Laser ablation allows the deposition of complex materials such as high temperature superconductor films and ceramic materials. Further, an ion implantation chamber can be provided to enable the incorporation of dopants into a sample. In addition, where a chemical vapor deposition process can be conducted at a temperature that is conducive to water ice, a chemical vapor deposition chamber can be included. These examples demonstrate the range of physical deposition chambers that can be included in the EBIL cluster tool.

In addition, there can be included chambers for removal of material from a sample. For example, a sputtering chamber in which, e.g., ions, such as Ar, Xe, etc., bombard a sample surface to remove material can be included. The ions are here generally in either a DC, AC or magnetron assisted plasma. A condensed ice layer produced in the cluster tool can be used as the masking layer to pattern the removal of an underlying substrate by Ar, Xe, or other ion. Because sputtering removes approximately equal amounts of ice mask and sample, the ice masks used for material removal must be at least as thick as the thickness of material to be removed from the underlying sample. Further, there can be included a chamber for reactive ion etching (RIE), utilizing reactive chemical radicals created in plasmas to chemically etch a sample. RIE and its derivatives have a better selectivity compared to sputtering processes. Many nanostructures, such as CNTs and graphene, can be etched using either sputtering or RIE with oxygen chemistries.

Additional EBIL cluster tool chambers can be included, e.g., focused ion milling (FIB) in a cluster tool that includes both a SEM and a FIB. Here an ice layer can be employed as a protective layer for fragile nanostructures. Before operating the FIB, an image of the sample can be taken to map the sample using the SEM beam so that it can be determined where to mill with the FIB. Such an SEM image conventionally causes significant damage to delicate nanostructures. The protective ice layer provided over nanodevices enables the initial mapping process in the manner described above without damage to the devices.

In addition, as explained above, it is to be recognized that the surface imaging and spatial mapping processes enabled by the EBIL sequence herein can be employed separately and alone if desired, without the inclusion of subsequent lithographic process steps. In other words, it is contemplated herein that the EBIL process and cluster tool can for many applications be employed specifically and solely for the purpose of imaging and mapping of a surface layer on a substrate and/or structures on the surface layer through an ice resist layer that prevents contamination from reaching the surface layer. The protective ice layer can be formed in the EBIL tool, with E-beam imaging conducted within the tool immediately following ice layer formation. If desired, processing of the substrate and/or patterning of the ice layer can subsequently be carried out, with additional imaging through the protective ice layer during and subsequent to the processing. The EBIL process thereby enables an E-beam imaging technique for viewing, mapping, and analyzing a surface and structures on the surface for imaging purposes alone, as well as prior to, during, and subsequent to a processing step or steps. For example, the imaging of SWCNTs through a condensed ice layer can employed as a non-invasive method for rapid quality control of the electrical integrity of nanodevices, even if such devices are formed, processed, and/or patterned in another tool.

Thus, the E-beam ice lithography method and cluster tool enable nano-device fabrication and processing in a manner that overcomes problems often faced in the design and production of nano-scale systems. Condensed, amorphous water ice can serve as a protective coating for detailed imaging and spatial mapping of a substrate surface while preventing contamination from reaching the surface, and then further serve as a resist for high resolution E-beam lithography. The properties of water ice allow direct application in a vacuum environment, conformal coating of complex three-dimensional structures, through-resist mapping and registration of nanostructures, and simple, contamination-free removal. A wide range of device and system configurations and properties that heretofore were unattainable are thereby rendered achievable by the EBIL methodology using only current technology.

It is recognized, of course, that those skilled in the art may make various modifications and additions to the processes of the invention without departing from the spirit and scope of the present contribution to the art. Accordingly, it is to be understood that the protection sought to be afforded hereby should be deemed to extend to the subject matter of the claims and all equivalents thereof fairly within the scope of the invention.

We claim:

1. A method for imaging a solid state substrate comprising:
condensing a vapor to an amorphous solid water condensate layer on a surface of a solid state substrate;
producing an image of at least a portion of the substrate surface by scanning an electron beam along the substrate surface through the water condensate layer; and
maintaining integrity of the water condensate layer during electron beam scanning to prevent electron-beam contamination from reaching the substrate during electron beam scanning.

2. The method of claim 1 further comprising first disposing on the substrate surface at least one structure before condensing a vapor on the substrate surface.

3. The method of claim 2 wherein disposing a structure on the substrate surface comprises fabricating the structure on the substrate surface.

4. The method of claim 1 further comprising first disposing a layer of electrically insulating material on the substrate surface before condensing a vapor on the substrate surface.

5. The method of claim 4 wherein the electrically insulating layer comprises a microelectronic material selected from oxide materials and nitride materials.

6. The method of claim 1 wherein producing an image of at least a portion of the substrate surface comprises producing an image of structures that are disposed on the substrate surface by scanning an electron beam over the structures while scanning the substrate surface.

7. The method of claim 1 wherein producing an image of at least a portion of the substrate surface comprises producing an image of lithographic pattern registration marks that are disposed on the substrate surface.

8. The method of claim 1 wherein producing an image of at least a portion of the substrate surface comprises mapping spatial coordinates of features of the substrate surface.

9. The method of claim 1 further comprising first disposing on the substrate surface at least one carbon nanotube before condensing a vapor on the substrate surface.

10. The method of claim 1 further comprising first disposing on the substrate surface at least one structure selected from micromachined cantilever and micromachined bridge before condensing a vapor on the substrate surface.

11. The method of claim 1 further comprising first forming in the substrate surface a feature selected from aperture and trench before condensing a vapor on the substrate surface.

12. The method of claim 1 wherein the solid-state substrate comprises graphene.

13. The method of claim 1 wherein the solid state substrate comprises a self-supported membrane having a peripheral support structure.

14. The method of claim 1 wherein the substrate comprises a structure selected from microelectronic substrate, wafer, and chip.

15. The method of claim 1 wherein the substrate comprises an atomic force microscope cantilever.

16. The method of claim 1 further comprising first forming on the substrate surface a carbon nanotube catalyst region and synthesizing at least one carbon nanotube from the catalyst region before condensing a vapor on the substrate surface.

17. The method of claim 16 further comprising first forming on the substrate surface at least one electrically conducting contact pad before condensing a vapor on the substrate surface.

18. The method of claim 16 wherein producing an image of at least a portion of the substrate surface comprises mapping spatial coordinates of at least one carbon nanotube on the substrate surface.

19. The method of claim 1 wherein substrate is maintained at a temperature that is less than about 130 K while condensing a vapor on the substrate surface.

20. The method of claim 1 wherein the vapor being condensed is supplied from a solid source.

21. The method of claim 1 wherein pressure local to the substrate is maintained at less than about $10^{-6}$ T while condensing a vapor on the substrate surface.

22. The method of claim 1 further comprising, after producing an image of at least a portion of the substrate surface, locally removing at least one selected region of the water condensate layer by directing an electron beam at the at least one selected region.

23. The method of claim 22 wherein directing an electron beam at the selected region comprises scanning the selected region with an electron beam patterning dose that is at least about one thousand times greater than the electron beam imaging dose.

24. The method of claim 22 wherein directing an electron beam at the selected region comprises scanning the selected region with an electron beam patterning dose that is at least about two orders of magnitude greater than the electron beam imaging dose.

25. The method of claim 22 wherein directing an electron beam at the selected region comprises scanning regions of the ice layer that are coincident with surface features that were previously spatially mapped during production of an image of at least a portion of the substrate surface.

26. The method of claim 22 wherein directing an electron beam at the selected region comprises scanning the selected region with an electron beam patterning dose that is at least about 1 $C/cm^2$.

27. The method of claim 22 wherein directing an electron beam at the selected region comprises scanning a plurality of selected regions to form a pattern of openings in the water condensate layer.

28. The method of claim 27 further comprising producing an image of the pattern of openings in the water condensate layer by scanning an electron beam along the substrate surface through the patterned water condensate layer.

29. The method of claim 28 further comprising, after producing an image of the pattern of openings in the water condensate layer, condensing a vapor to an amorphous solid water condensate layer on the patterned condensate layer.

30. The method of claim 22 further comprising:
    depositing a material layer on top of the water solid water condensate layer and on any substrate surface exposed at the at least one selected region; and
    removing the water condensate layer and regions of the material layer that were deposited on top of the solid water condensate layer, leaving a patterned material layer on the substrate.

31. The method of claim 30 wherein depositing a material layer comprises sputter deposition of a material.

32. The method of claim 30 wherein depositing a material layer comprises vapor deposition of a material layer.

33. The method of claim 30 wherein depositing a material layer comprises depositing an electrically conducting material layer.

34. The method of claim 30 wherein removing the water condensate layer and regions of the material layer that were deposited on top of the water condensate layer comprises a process of lift-off of the material layer regions as the water condensate layer is removed.

35. The method of claim 30 wherein the vapor condensation, localized removal, and material layer deposition are all carried out in a single cluster of chambers.

36. The method of claim 1 further comprising minimizing removal of the water condensate layer while producing the image by scanning the substrate surface with an electron beam imaging dose of less than about 100 $\mu C/cm^2$.

* * * * *